United States Patent [19]

Fahim

[11] Patent Number: 5,071,658

[45] Date of Patent: Dec. 10, 1991

[54] INTRAPROSTATIC INJECTION OF ZINC IONS FOR TREATMENT OF INFLAMMATORY CONDITONS AND BENIGN AND MALIGNANT TUMORS OF THE PROSTATE

[76] Inventor: Mostafa S. Fahim, 500 Hulen Dr., Columbia, Mo. 65203

[21] Appl. No.: 556,632

[22] Filed: Jul. 23, 1990

Related U.S. Application Data

[62] Division of Ser. No. 214,773, Jul. 5, 1988, Pat. No. 4,946,688.

[51] Int. Cl.[5] .................. A61K 31/60; A61K 31/315; A61K 31/555; A61K 33/32
[52] U.S. Cl. .................................... 424/643; 514/159; 514/184; 514/494
[58] Field of Search ................ 424/643; 514/159, 184, 514/494

Primary Examiner—Stanley Friedman
Attorney, Agent, or Firm—Grace J. Fishel

[57] ABSTRACT

A method of treating the prostate by intraprostatic injection of zinc ions in a concentration effective to increase the amount of prostatic antibacterial factor and to inhibit the rate of prostatic growth. The treatment is applied to patients with prostatitis, to patients with benign adenomatous hyperplasia of the prostate after prostatic resection and to patients with early prostatic carcinoma as an alternative to surgery as needed to provide long-term remission. The treatment is also applied prophylactically to prevent the development of prostatitis, particularly in males of advanced age.

5 Claims, No Drawings

INTRAPROSTATIC INJECTION OF ZINC IONS FOR TREATMENT OF INFLAMMATORY CONDITONS AND BENIGN AND MALIGNANT TUMORS OF THE PROSTATE

This is a division of application Ser. No. 07/214,773, filed July 5, 1988, now U.S. Pat. No. 4,946,688.

BACKGROUND OF THE INVENTION

Inflammation and benign and malignant tumors of the prostate afflict a large number of adult males. The etiology of these conditions is generally unknown, but may involve the normal aging process and associated alterations in hormonal balance. Mankind is not unique in this regard and other animals with a compact or solid prostate, such as dogs, suffer comparable disease states.

Chronic prostatitis is the most common chronic infection in adult males. It has been claimed to afflict about 35% of all male subjects at sometime during their lives. The typical patient is a middle-aged or elderly male referred for evaluation of repeated episodes of cystitis and pyelonephritis or epididymitis. Benign adenomatous hyperplasia of the prostate is also common malady seen in men over age 50 while adenocarcinoma of the prostate accounts for the ajority of malignancies in men over age 65.

Chronic prostatitis can be classified into: (1) non-specific prostatitis, (2) specific prostatitis due in to infection with bacteria or fungi and (3) granulomatous, which may be non-specific (with unknown cause) or allergic, which is usually accompanied by some general allergic disease as bronchial asthma. Although granulomatous prostatitis is very rare, it should be differentiated from prostatic carcinoma.

The pathogenesis of the infectious types of prostatitis often is unclear. Possible routes of infection include: ascending urethral infection, reflux of infected urine into the prostatic ducts that empty into the prostatic urethra, invasion by rectal bacteria via direct extension or lymphogenous spread and hematogenous infection. The causative agents in chronic bacterial prostatitis are similar in type and prevalence to those responsible for urinary tract infection. Infection caused by common strains of *Escherichia coli* are predominant, although infections caused by species of Proteus, Klebsiella, Enterobacter, Pseudomonas and other less common types of gram-negative organisms are sometimes found. Mixed infections caused by two or more strains or classes of bacteria are not rare.

Opinions vary concerning the role of gram-positive bacteria as causative agents in chronic prostatitis. All agree that enterococcus is an important pathogen, whose persistence in the prostate causes relapsing urinary infections but whether other common gram-positive organisms such as micrococci, Staphylococci, Streptococci and diphtheroids are frequent or important prostatic pathogens is highly debatable.

Until the present time the treatment of chronic bacterial prostatitis has been mostly unsatisfactory. This is because the bacteria in prostatic fluid is a major cause of urinary infections in male patients who become symptomatic only when the bladder is infected. Most treatments involve maintaining the patient on a continuous low dosage of antimicrobial agent, which produces bactericidal bladder urine and prevents bacteria from infecting the bladder urine. This however does not kill the bacteria in the prostate who are protected from the action of the antimicrobial agent which cannot cross the prostatic epithelium in an effective concentration.

It is known that prostatic secretions of normal subjects contain much greater antibacterial activity than that found in men with proven bacterial prostatitis. This raises the possibility that a prostatic antibacterial factor might serve as a natural defense against prostatic and urinary infections. Purification an crystallization of prostatic antibacterial factor has revealed that its antibacterial activity is related to its concentration of zinc. Attempts to alter the level of zinc in the prostatic fluid by the oral administration of zinc preparations have failed.

As to the treatment of non-infectious prostatitis, benign adenomatous hyperplasia of the prostate and adenocarcinoma of the prostate, it is known that prostatic growth is under the control of androgen receptors in the prostate. The androgen receptors are stimulated by 5 a-dihydrotestosterone (DHT) which is produced in the prostate by enzymatic conversion of testosterone, which in turn is secreted by the testicular Leydig cells. While the pathogenesis of the above-mentioned conditions is generally unknown and as to latter two conditions, the definitive therapy is surgical, a treatment which inhibits the androgen receptors by blocking them or interfering with the enzymatic conversion of testosterone to DHT might have a beneficial effect by preventing reactivation of the disease or by providing long-term regression and, in the case of prostatic carcinoma, offer an alternative to surgery.

In view of the above, there is a need for an for an effective means of increasing the amount of prostatic antibacterial factor and for controlling the rate of prostatic growth by inhibiting the androgen receptors in the prostate. It is therefore an object of the present invention to provide a method of treatment for inflammatory conditions and benign and malignant tumors of the prostate by increasing the amount of prostatic antibacterial factor secreted by the prostate and by inhibiting the androgen receptors which control the rate of prostatic growth. Other objects and features of the invention will be in part apparent and in part pointed out hereinafter.

The invention accordingly comprises the methods hereinafter described and their equivalents, the scope of the invention being indicated in the following claims.

SUMMARY OF THE INVENTION

The present invention relates to a method of treating the prostate by intraprostatic injection of zinc ions in a concentration effective to increase the amount of prostatic antibacterial factor and to inhibit the rate of prostatic growth. The treatment may be applied to patients with prostatitis, to patients with benign adenomatous hyperplasia after surgery to prevent reactivation of the disease, to patients with early adenocarcinoma of the prostate as an alternative to surgery, and to patients prophylactically to prevent the development of prostatitis, particularly to males of advanced age, as patients with prostatic carcinoma usually have a history of prostatitis.

DETAILED DESCRIPTION OF THE INVENTION

I. Diagnosis of Chronic Prostatitis

The clinical picture of chronic prostatitis is highly variable and inexact. Indeed the symptoms, signs and physical findings alone cannot differentiate the common forms of chronic prostatitis—namely, bacterial, nonbacterial and prostatodynia. Likewise x-ray studies and cystotrethroscopy do not confirm specifically the diagnosis of chronic prostatitis. Chronic bacterial prostatitis is one of the most common causes of relapsing urinary tract infection in men. History of prior bouts of acute prostatitis may be present. Indeed some men present only urinary tract infection and asymptomatic bacteriuria is found incidently.

The majority of patients complain of varying degrees of irritative voiding symptoms, including dysuria, urinary urgency and frequency together with pain perceived in various sites (perineal, low back, supra pubic, scrotal, penile or even in the inner thighs). Urinary symptoms predominate because of associated urinary tract infection, e.g., cystitis and posterior urethritis. Obstructive symptoms in the form of difficulty, weak stream and dribbling may be due to the associated fibrosis and contracture of the bladder neck and posterior urethra. Some experience post ejaculatory pain and may notice intermittent hematospermia. Other sexual symptoms such as weak erection, premature ejaculation and impotence are mostly psychosomatic complications or due to associated seminal vesiculitis. Rectal palpation discloses no specific or characteristic findings and a tender or boggy prostate is not diagnostic. Evidence of an associated recurrent or chronic epididymitis sometimes is obtained from a medical history or noted on physical examination.

Examination of the expressed prostatic secretion (E.P.S.) is an important aid in diagnosis but can be misleading. Inflammatory cells whose source is not the prostate but the urethra (urethritis, urethral stricture, diverticulum and condylomas) can contaminate the prostatic expressate as it passes through the urethra during massage. To overcome this problem, the microscopic appearance of prostatic expressate can be compared to smears of the spun sediment of the first voided 10 ml of urine (urethral specimen) and the mid stream urine (bladder specimen) to localize the site of inflammatory response. The most accurate and useful method of establishing the diagnosis of bacterial prostatitis is the performance of simultaneous quantitative bacteriologic culture of the urethra, bladder urine and E.P.S. The voided urine and prostatic secretions are collected as segmented specimens—the first voided 10 ml ($VB_1$), the mid stream aliquot ($VB_2$), the prostatic expressate obtained by prostatic message (E.P.S.) and the first voided 10 ml immediately after prostatic massage ($VB_3$). All specimens are cultured quantitatively by surface streaking onto blood and Mac Conkey agar. The diagnosis of prostatic infection is confirmed when the quantitative bacterial colony counts of the prostatic specimens (E.P.S. and $VB_3$) significantly exceed those of the urethral ($VB_1$) and bladder ($VB_2$) specimens.

Opinions differ concerning what constitutes an abnormal number of leucocytes in the prostatic secretions. Most agree that more than 20 white blood cells/high power field of a microscope (H.F.P) is abnormal. Some prefer the criterion of more than 15 and others believe that more than 10 white blood cells/H.P.F. represent leucocytosis.

The presence of increased numbers of lipid laden macrophages (oval fat bodies) in prostatic fluid are also diagnostic of bacterial prostatitis as they localize the site of inflammation to the prostate, since they are not found in urethral exudate.

Prostatic biopsy shows increased fibrous tissue stoma with infiltration of the stomas and acini to a varying degree by chronic inflammatory cells (lymphocytes and plasma cells) which may be scattered or in foci. Polymorphonuclear leucocytes are also found, in foci, in some cases and indicate focal acute exacerbation. Histologic examination is necessary to diagnose the unusual forms of chronic prostatitis, e.g., granulomatous, but the use of prostatic biopsy is seldom justified in the diagnosis of the usual case of chronic prostatitis. This is because the infection is usually focal and errors in sampling are significant. Also, factors other than infectious pathogens produce a similar histologic picture, e.g. senile prostatic changes.

II. Diagnosis of Benign Prostatic Hypertrophy

Symptoms of bladder outlet obstruction may include progressive urinary frequency and urgency, nocturia as a result of incomplete emptying and rapid refilling of the bladder, hesitancy and intermittency of the urinary stream due to fluttering occlusion of the prostatic urethra, decreased size and force of the urinary stream, sensations of incomplete emptying, terminal dribbling, almost continuous overflow dribbling, or complete urinary retention. Rectal examination may be misleading; a prostate that is small by rectal examination may yet be sufficiently enlarged to cause urethral obstruction. Hematuria is caused by congestion of superficial veins of the prostatic urethra and trigone which rupture while the patient is straining to void. Burning on urination and chills and fever indicate urinary infection. Episodes of acute complete urinary retention may follow prolonged attempts to retain urine, exposure to cold, immobilization, or ingestion of alcohol. The distended urinary bladder is palpable on physical examination. Prolonged urinary retention, partial or complete, will result in progressive renal failure and azotemia.

Benign prostatic hypertrophy with bladder outlet obstruction is suspected on the basis of the above-mentioned symptoms and signs. Rectal examination usually discloses an enlarged gland with a rubbery consistency and, frequently, loss of the median furrow. An indurated and tender prostate suggests prostatitis, while a stony hard nodular prostate usually indicates carcinoma or, less likely, prostatic calculi. An excretory urogram may disclose upward displacement of the terminal portions of the ureters (fishhooking) and a defect at the base of the bladder compatible with prostatic enlargement. The postvoiding cystogram will provide an index of residual urine, which should normally be less than 10 ml. Catheterization provides a measurement of residual urine and permits preliminary drainage to stabilize renal function and afford adequate control of urinary infection. Cystoscopy permits estimation of the size of the gland and the appropriate surgical approach, plus an opportunity to differentiate between contracture of the vesical neck, chronic prostatitis, and other obstructive phenomena. Instrumentation should be avoided until there is a commitment to definitive therapy, since manipulation may induce trauma and infection, complicating management.

III. Diagnosis of Prostatic Carcinoma

Prostatic carcinoma is generally slowly progressive and may cause no symptoms. Late in the course of the disease, symptoms of bladder outlet obstruction, hematuria, and pyuria may appear. Metastas s to the pelvis and lumbar spine may cause bone pain. Stony hard induration of the prostate raises the suspicion of prostatic malignancy and must be distinguished from granulomatous prostatitis, prostatic tuberculosis, prostatic calculi, and other more unusual prostatic diseases. The firm and nodularly irregular prostate is pathognomonic of prostatic carcinoma, later exhibiting extension of induration and fixation of the gland to the rectum and the lateral pelvic walls.

IV. Treatment

In accordance with the present invention, a patient diagnosed with chronic prostatitis, benign prostatic hypertrophy, early prostatic cancer or the like is treated, one or more times, by intraprostatic injection with an effective amount of zinc ions to increase the amount of prostatic antibacterial factor secreted by the prostate and to inhibit the rate of prostatic growth. A suitable source of zinc ions for this purpose are water soluble zinc salts formed with a physiologically acceptable anion such as zinc acetate, zinc ascorbate, zinc chloride, zinc citrate, zinc gallate, zinc gluconate, zinc lactate, zinc salicylate, zinc sulfate, zinc tannate, zinc tartrate and the like including the salts of amino acids such as zinc lysate, zinc arginate and zinc histidinate, as well as mixtures thereof.

The volume of solution injected should be selected to avoid rupture of the prostate and depends on the species of animal undergoing treatment and the size of the subject's prostate. In the case of humans, a volume in the order of about 0.25 cc to 2 cc, preferably about 0.5 cc to 1 cc is suitable, whereas the volume with other species can be determined in view of the above-mentioned parameters.

When the volume of the injection is in the above-mentioned ranges, the concentration of the zinc solution injected into the prostrate effective to raise the amount of prostatic antibacterial factor secreted by the prostate and to inhibit the rate of prostatic growth is about 0.25% to 20% by weight, preferably 1% to 2% by weight of $ZnSO_4 \cdot 7H_2$) or an equivalent amount of some other suitable source of zinc ions. To aid diffusion of the zinc ions in the prostate and/or to avoid damaging the prostatic tissue, the solution of zinc ions injected into the prostate may be neutralized to about pH 7 if the zinc salt does not precipitate. Of the salts mentioned above, zinc gluconate is particularly adaptive to use in this manner, along or in combination with those amino acid zinc salts which do not precipitate at pH 7 such as lysine, arginine and histidine.

Depending on the condition being treated, the prostate may be accessed for injection by transurethral, transrectal, suprapubic, retropubic or perineal techniques. While the work reported in the following examples was performed by injection of the zinc ions into the prostate with a needle, it is to be understood that other means of penetration may also be employed and may be preferred, for example, in the treatment of prostatic carcinoma as a means to avoid possible metastases.

In the case of chronic prostatitis, whether bacterial or non-bacterial in origin, the present method is effective as the sole treatment. With benign prostatic hypertrophy, treatment is usually surgical, followed by intraprostatic injection of zinc ions. Transurethral prostatic resection is effective in smaller benign enlargements but larger benign prostates may be managed by open surgery using the suprapubic, retropubic or perineal techniques that permit enucleation of the adenomatous tissue from within the surgical capsule. Radial prostatectomy is the treatment of choice with prostatic cancer, sometimes with bilateral orchiectomy. The present invention can be used in the treatment of early prostatic cancer without surgery and repeated as needed to maintain long-term regression. In some instances, the present method may be applied prophylactically, for example to patients of advanced age, as patients who develop prostatic cancer usually have a history of prostatitis.

Throughout the following examples 1–3, a group of 78 patients having chronic prostatitis were subdivided into four treatment groups:

a. 36 patients treated with intraprostatic injection of zinc sulfate.
b. 12 patients received oral zinc sulfate.
c. 12 patients received oral zinc acetate
d. 18 patients treated with antibacterial agents together with prostatic message.

The treatment applied to the patients in group (a) described in Example 1 is in accordance with the present invention while the treatments applied to groups (b), (c) and (d) described in Examples 2–3 were for purposes of comparison.

The age of the patients diagnosed with chronic prostatitis varied from 24–60 years. The average age was 39 years. As is shown in Table 1 the commonest age for incidence of chronic prostatitis was in the 4th decade of life followed by the 5th and 6th decades.

TABLE 1

| Age in years | Age distribution No. of cases | % |
|---|---|---|
| 21–30 | 9 | 11.5 |
| 31–40 | 38 | 48.8 |
| 41–50 | 21 | 26.9 |
| 51–60 | 10 | 12.8 |
| Total | 78 | 100 |

The patients were assessed as follows:

I. Full clinical assessment including a. history taking
b. general examination
c. abdominal examination including external genitalia, together with rectal examination.

Symptomatology

As shown in Table 2, pain in its different forms, either pain on voiding (smarting micturition), supra pubic, urethral, low back pain and perineal deeply seating pain were the commonest presenting symptoms. Frequent micturition, meaning that the patient voided more than five times during the day and was also awakened at night, was common, while hematuria and urgency were rare. Obstructive symptoms as well as sexual troubles such as weak erection or complete loss of erection were also less common. The duration of the symptoms varied from 7 months to 11 years.

TABLE 2

| Complaint | Symptoms No. of Cases | Percentage |
|---|---|---|
| Pain: | | |
| Smarting micturition | 48 | 61.5 |
| Urethral | 28 | 35.9 |
| Suprapubic | 25 | 32 |
| Low back | 24 | 30.8 |
| Perineal | 22 | 28.2 |
| Obstructive symptoms: | | |
| Difficulty micturition | 22 | 28.2 |

TABLE 2-continued

| Complaint | Symptoms No. of Cases | Percentage |
|---|---|---|
| Weak stream | 7 | 9 |
| Dribbling | 6 | 7.7 |
| Urinary: | | |
| Frequent micturition | 44 | 56.4 |
| Urgency | 8 | 10.2 |
| Hematuria | 3 | 3.8 |
| Sexual: | | |
| Weak erection | 25 | 32 |
| Premature ejaculation | 12 | 15.4 |
| Impotence | 12 | 15.4 |
| Painful ejaculation | 9 | 11.4 |

Clinical examination

In more than half of the cases, the prostate on rectal examination was soft and smooth and in less than half of the cases, it was tender. Nodularity, finely granular as well as boggy, and enlarged prostates were also found.

TABLE 3

| Clinical findings | Clinical examination No. of cases | Percentage |
|---|---|---|
| Soft and smooth | 41 | 52.5 |
| Tender prostate | 37 | 47.5 |
| Nodular | 15 | 19.2 |
| Finely granular | 12 | 15.4 |
| Boggy and enlarged | 9 | 11.4 |

II. Radiologic examination

Plain x-ray of the abdomen and pelvis was done for all patients to show any stone or calcification in the urinary tract or prostatic calculi. In the great majority of patients with chronic prostatitis, no abnormal findings were detected. One case, out of the 78 patients with chronic prostatitis, had stone bladder, which necessitated cystolithotomy. Two cases had biharzial calcification of the bladder and one of them also had calcification of the seminal vesicles. One case treated with oral zinc sulfate had prostatic calculi.

Excretory urography was done for patients not responding to treatment to exclude associated lesions of the urinary tract. It was also done on all patients with chronic cystitis. Radiologic evidences of chronic pyelonephritis were found in two cases. One case revealed contracted bladder which was proved by measuring bladder capacity and another proved to have senile prostatic enlargement with prostatic indentation.

III. Cystoscopic examination

Cystoscopic examination was performed for patients with suspicious bilharzial ulceration or other pathological lesions of the bladder under general anesthesia and complete aseptic precautions. The cystoscope was of the fibro-optic type (Wolf) with a visualizing angle 160 degrees. Sterilized water, which was boiled and allowed to cool to room temperature in sterile bottles, was used for bladder irrigation.

IV. Laboratory examination a Examination of expressed prostatic secretion (E.P.S.): The glans penis was cleaned with 70% alcohol and then allowed to dry. Gentle prostatic massage was done while the patient was lying on his back, until a secretion appears at the external urethral meatus, where a drop was taken for direct microscopic examination, on a clean glass slide. The slide was covered with a clean 22 mm glass cover and the wet preparation was examined for pus cells, R.B.G., parasitic infestation, e.g., trichomonas or bilharzia ova, and the presence of prostatic deposits, i.e., refractile fat bodies.

b. Culture of the prostatic secretion: Using a bacteriologic loop which was previously sterilized by heating in a flame until red and then allowed to cool at room temperature, a loop full of the E.P.S. was immediately streaked on blood agar plates. The same procedure was also done on Mac Conkey's bile salt agar. The plates were incubated aerobically at 37 degrees C. and examined after 24 hours. If there was no growth, they were left for another 24 hours. If there was still no growth after 48 hours, they were reported as no growth. If growth appeared, identification of the offending pathogens was carried out.

c. Urine culture: A mid stream urine sample was collected aseptically in a sterile test tube after cleaning the glans penis as described previously. A portion of the sample was streaked on blood agar and Mac Conkey's bile salt agar plates. The plates were incubated aerobically at 37 degrees and examined after 24 hours or 48 hours as previously mentioned before growing organisms were identified.

Bacteriological identification was done as follows:

1. Morphologic characteristics a. Cultural characteristics: The colonies were examined after 24 hours incubation at 37 degrees C. on blood agar and Mac Conkey's bile salt agar. In bacterial identification particular attention was paid to their shape, size, color, consistency, e.g., viscid, friable, membranous or the like, surface, e.g., smooth, granular, dull or glistening, differentiation, i.e., differentiated into central and peripheral zones and the presence of hemolysis and odor.

b. Staining: A film was stained with gram stain for differentiation of different organisms according to their stained characteristics, i.e., gram positive or gram negative, and also according to their shape, i.e., bacilli or cocci, arrangement of the organisms and so forth.

2 Biochemical reactions

Carbohydrate fermentation: Triple sugar iron agar was used for the differentiation of gram negative enteric bacilli by means of their ability to attack dextrose, lactose and sucrose to liberate sulfides. The media (T.S.I) contained 20,000 g peptone, 5,000 g sodium chloride, 10,000 g lactose, 10,000 g sucrose, 1,000 g dextrose, 0.2 g ferrous ammonium sulfate, 0.2 g sodium thiosulfate, 0.025 g Phenol red and 13,000 g agar per liter of distilled water. T.S.I. agar slants were inoculated from suspicious colonies and read after 24 or 48 hours incubation. Acid formation was indicated by yellow color change of the Phenol red indicator. Thus the sugar fermenting organisms, e.g. coliforms, paracolon and Proteus, were distinguished by the development of yellow slants on T.S.I. agar from other species.

Amino acid breakdown: The indol test demonstrates the ability of certain bacteria to decompose the amino acid tryptophane to indol which accumulates in the medium. Indol is then tested for by colormetric reaction with dimethylamino benzaldehyde. The following medium was used for growth: 20 g peptone, 5 g sodium chloride in 1 liter distilled water. the pH was adjust to 7.4 and the medium was sterilized by autoclaving at 121 degrees C. for 15 minutes. The medium was inoculated from culture and incubated at 37 decrees C for 48 hours. Then 0.5 ml Kovac's reagent, was added and the mixture shaken gently. A red color indicated a positive reaction.

Urease test: The occurrence of urease secreting bacteria can be tested for by growing the organism in the presence of urea and testing for the alkali ($NH_3$) production by means of a suitable pH indicator. The following medium was used: 1 g peptone, 5 g NaCl, 2 g dipotassium hydrogen phosphate, 26 ml Phenol red (1 g in 500 ml aqueous solution), 20 g agar in 1 liter distilled water. The pH was adjusted to 6.8 and the medium was autoclaved at 121 degrees C. for 15 minutes. When it had cooled to about 50 degrees C. a sterile solution of glucose was added to give a final concentration of 0.1% and 100 ml of a 20% solution of urea which had been previously sterilized by filtration was added. The medium was then tubed as deep slopes. The slopes were inoculated heavily over the entire surface and incubated at 7 degrees C. They were examined after 4 hours and after over night incubation. No tube was described as negative growth until after 4 days of incubation. Urease positive cultures produced a purple-pink color due to change in the color of the indicator.

Citrate utilization test: Those organism that have the ability to utilize citrate as the sole carbon and energy source of nitrogen were identified by growth in Simmon's citrate agar: 5.0 g NaCl, 0.2 $MgSO_4$, 1 g $NH_4H_2PO_4$, 1 g $KH_2PO_4$, 6.0 g $Na_3C_6H_5.2H_2O$, 20 g washed agar and 1 liter distilled water. Bromothymol blue (1:500 aqueous solution) in an amount of 40 ml. was added as an indicator and the pH adjusted to 6.8. The medium was sterilized by autoclaving and was poured as slopes. The slopes were inoculated from a saline suspension of the organism to be tested and incubated for 96 hours at 37 degrees C. The result was described positive if blue color and streak of growth appeared but was considered negative if the original green color persisted and no growth occurred.

Coagulation test: A glass slide was divided into two sections with a grease pencil. A drop of normal saline was dropped onto each area. A small amount, e.g. one or two colonies from an agar plate of the tested strain, was emulsified in each of the two drops to make a smooth suspension. A drop of human plasma was added to one of the drops and stirred gently with a wire. Clumping of the organisms resulted if the strain was coagulase positive because fibrinogen precipitates on the cell surface causing them to stick together.

Motility test: For detection of motility, the organisms were inoculated in semisolid agar with a straight wire loop, making a single stab down the center of the tube to about half the depth of the medium. The tubes were then incubated at 37 degrees C. for 24 hours. Non motile bacteria generally gave growths that were confined to the stab line, had sharply defined margins and left the surrounding medium clearly transparent. The motile bacteria typically gave diffuse, hazy growths that spread throughout the medium rendering it slightly opaque and reaching the walls of the tube after a few hours and the foot of the tube after one or two days. Non motile strains that yield motile variants, formed a discrete line of growth along the stab and diffuse growth then fanned out from one or two points.

The following media were used for the cultures:

1. Blood agar: The medium was prepared by adding sterile blood to a sterile nutrient agar that had been melted and cooled to 55 degrees C. The amount of blood can be varied from 5-50%, with the most usual concentration being 10%. If the medium is 10% blood and used as a single layer, a fairly thick layer is required to prevent excessive drying during incubation. Such a layer, however, is almost opaque when viewed by transmitted light and hemolysis is difficult to be seen. Double layer blood agar overcomes this difficult wherein a thin layer of melted nutrient agar, about 7 ml for a 4 inch petri dish, is poured and allowed to set. Then a similar thin layer of 10% blood agar is poured on top of the first layer and any bubbles are easily removed by drawing a Bunsen flame quickly across the surface of the medium in the dish.

Mac Conkey's medium: This useful medium for the cultivation of enteric bacteria consists of bile salts to inhibit non-intestinal bacteria and lactose with neutral red to distinguish lactose-fermenting coliforms from non-lactose fermenting salmonella and dysentery groups. The constituents are as follows: 20 g peptone, 5 g sodium taurocholate, 20 g agar, 3.5 ml neutral red solution (2% in 50% ethanol), 100 ml lactose (10% aqueous solution) in 1 liter water. It is prepared by dissolving the peptone and taurocholate in the water by heating, adding the agar and dissolving it in a steamer or autoclave. The solution is cleaned by filtration and the pH is adjusted to 7.5. Lactose and the neutral red, which should be shaken and well mixed before use, are then added and the mixture heated in an autoclave with "free steam" (100 degrees C.) for one hour, then at 115 degrees C for 15 minutes. It is then poured in plates. The medium should be a distinct reddish-brown color and assumes a rose-pink color in the presence of acid. Since the neutral red tends to fade after storage for any length of time, the medium should be prepared shortly before it is used.

Prostatic biopsy

While the patient was in the lithotomy position, and without anesthesia or analgesia, the scrotum and penis were retracted ventrally, The perineum was cleaned with savlon and sterilized with 70% alcohol. A gloved index finder of the left hand, after good lubrication, was introduced into the rectum to guide the tip of the needle (Silverman) towards the prostate. The needle was introduced using the right hand slightly lateral to the midline and directed toward the prostate and after localizing the point where the biopsy was to be taken, the left hand is removed and its glove is replaced by another sterile one. The biopsy was taken and the needle was withdrawn. The piece of tissue obtained was preserved immediately in formalin (50% solution). The perineum was then supported for a few minutes to prevent bleeding from the site of needle puncture.

A film was made from the biopsy tissue, stained with Hematoxylin and Eosine stains. Histological examination was done using the low and high power of a normal microscope.

The biopsies revealed that there was an increase of fibrous tissue stromas in most cases. Chronic inflammatory cells, either scattered or in foci and mainly lymphocytes and plasma cells, were found in many cases. Polymorphonuclear leucocytes were seen in some cases.

Estimation of serum zinc concentration: A sampling was taken before zinc injection by aspirating 10 ml blood, usually from the antecubital vein, regardless of the fasting state. Disposable syringes were used with wide bore needles. The needle was removed and the blood sample was poured gently on the side of a previously prepared test tube.

Blood samples were left to clot at room temperature for about one hour. The serum was poured into a clean prepared Wassermann tube. The latter was centrifuged at a rate of 3000 R.P.M. for 10 minutes. Clean serum was transferred into another clean prepared Wassermann tube, using a clean Pasteur pipette. The tube was sealed using a parafilm adhesive tape, then it was frozen until estimation of zinc was carried out.

Preparation of glassware: For atomic absorption work all glassware was thoroughly cleaned with warm water and rinsed thoroughly with deionized water. It was then dried by leaving it overnight inside an incubator at 37 degrees C.

The apparatus: The apparatus was a PYE Unicam S.P. 1900 double bean, digital display atomic absorption spectrophotometer.

Preparation of solution for standard curve: Hydrous zinc sulfate powder was used for this purpose, together with normal saline (0.9% NaCl). Different concentrations were prepared by preparing different weights of the zinc sulfate and dissolving it in the saline, in a previously prepared tube as discussed above.

Standard curve: The absorbance (optical density) of different samples (different concentrations of zinc) were estimated by absorption spectrophotometry. A standard curve was obtained by plotting the optical density against concentration.

Preparation of samples: The serum samples were diluted by adding 0.5 ml serum to 4.5 ml normal saline. The dilution was 1:10 and done in a dry test tube prepared as described before. A pipette was used and the tubes were shaken well to mix the contents.

Analysis: Using the apparatus described above, the optical density of each sample was estimated. Three readings were taken for each sample and the average was calculated. Using the standard curve, the relative concentration in the diluted samples was then estimated and the concentration in micrograms per milliliter (P.P.M.) was calculated by multiplying the relative concentration by the dilution factor. Concentration in mg/100 ml was obtained by multiplying the results by 100.

EXAMPLE 1

Thirty-six patients with chronic prostatitis were treated as follows:

Before therapy, a prostatic smear of expressed prostatic secretion (E.P.S.) was taken and examined under a microscope. The results are tabulated in Table 4. More than 15 pus cells per high power field of microscope (H.P.F.) was considered to be significant.

TABLE 4

| Prostatic smear before therapy | | |
|---|---|---|
| No. of pus cells/H.P.F. | No. of cases | % |
| 15-50 | 9 | 25 |
| 50-100 | 15 | 41.7 |
| above 100 | 12 | 33.3 |
| Total | 36 | 100 |

Bacteriologic studies

A urine sample was cultured aerobically on blood agar and Mac Conkey's media. No growth of any organism was found in more than two thirds of the cases. *Escherichia coli* was found in 4 out of the 36 cases, while enterococci was found in 2 cases.

TABLE 5

| Urine culture before therapy | |
|---|---|
| Organisms | No. of cases |
| No growth (after 48 hours) | 30 |
| E. coli | 4 |
| Enterococci | 2 |
| Total | 36 |

The same organisms were found in the prostatic fluid culture discussed below, proving that the source of infection was the prostate.

Prostatic fluid culture

The expressed prostatic secretion was also cultured aerobically on blood agar. No growth of any organisms was obtained in 15 out of the 36 cases. E. coli was found in 11 cases, making it the most common organism found. Other gram negative species were also found, but were uncommon as seen in the Table 6. Enterococci were found in 5 cases.

TABLE 6

| Prostatic fluid culture before therapy | |
|---|---|
| Organisms | No. of cases |
| No growth (non-bacterial prostatitis) | 15 |
| E. coli | 11 |
| B. proteus | 2 |
| Enterococci | 5 |
| Staphylococcus aureus | 2 |
| E. coli + pseudomonas pyocyaneous | 1 |
| Total | 36 |

Each patient was then treated as follows: While the patient was in the lithotomy position, and without anesthesia or analgesia, the perineum was sterilized with 70% alcohol. As described above, a Silverman needle was introduced, just lateral to the midline, and was pushed by the right hand, guided by the index finger of the left hand in the rectum. When its tip was felt inside the prostate, the left index finger was withdrawn from the rectum, the glove of the left hand was replaced by a sterile one and the stylet of the needle was removed. Then 0.5 ml of sterile hydrous zinc sulfate ($ZnSO_4 \cdot 7H_2O$), already prepared in a sterile disposable syringe, was injected through the needle to inside the prostate. The needle was withdrawn. At injection, the patient's reactions to injection, e.g., pain, vomiting, collapse, pulse, blood pressure and the like were noted.

Two different concentrations of zinc sulfate were used: 1% $ZnSO_4 \cdot 7H_2O$ for 20 patients and 0.1% $ZnSO_4 \cdot 7H_2O$ for 16 patients. The stock solution was preserved in a refrigerator at 4 degrees C.

Before the second injection and after one week of intraprostatic injection of 0.5 ml zinc sulfate, each patient was interrogated as regards subjective symptoms, improvement or increased symptoms and any complications and a prostatic smear was taken. The number of leucocytes per high power field was found to be normal (less than 15/H.P.E.) in 2 cases, and the patients symptoms were quite improved. All of the other patients showed improvement and the number of pus cells decreased as seen in Table 7. No great difference was found between the results of treatment with 1% or 0.1% zinc sulfate and hence the two groups were grouped together.

TABLE 7

| Prostatic smear after first injection | | |
|---|---|---|
| No. of leucocytes/H.P.E. | No. of cases | % |
| Within normal | 2 | 5.6 |
| 15-50 | 22 | 61.1 |
| 50-100 | 8 | 22.2 |
| above 100 | 4 | 11 |
| Total | 36 | 100 |

The second injection was given using the same amount and the same concentration of zinc sulfate as the first injection, using the same procedure.

After the second injection of zinc sulfate, most of the patients exhibited marked subjective improvement, direct prostatic fluid examination showed that the number of leucocytes became within normal in more than half of the cases as shown in Table 8.

TABLE 8

| Prostatic smear after second injection | | |
|---|---|---|
| No. of leucocytes/H.P.F. | No. of cases | % |
| Within normal | 20 | 55.5 |
| 15-50 | 11 | 30.6 |
| 50-100 | 5 | 14 |
| Total | 36 | 100 |

Before the third injection, 10 ml blood was obtained for estimation of serum zinc again after two injections with zinc. Full interrogation with the patient was carried out again and a prostatic smear was obtained and examined. The third injection was done using the same concentration, the same amount and the same maneuver.

The patients showing improvement after the first and second injection were not given the third injection hence only 34 patients received the third injection.

One week after the third injection more than 50% of patients exhibited marked subjective and objective improvement. Their expressed prostatic secretions were examined by direct wet preparation and the results are tabulated in Table 9.

TABLE 9

| Prostatic smear after third injection | |
|---|---|
| No. of leucocytes/H.P.F. | No. of cases |
| Within normal | 20 |
| 15-50 | 14 |

As shown in Table 10, a correlation is seen in the number of leucocytes in prostatic smear before treatment (1), after first injection (2), second injection (3) and third injection (4).

TABLE 10

Correlation of number of leucocytes in prostatic smears before treatment, after first, second and third injections.

| No. of leucocytes/ H.P.F. | Before treatment (1) | After first injection (2) | After second injection (3) | After third injection (4) |
|---|---|---|---|---|
| Within normal (not more than 15/H.P.F.) | — | 2 | 20 | 20 |
| 15-50 | 9 | 22 | 11 | 14 |
| 50-100 | 15 | 8 | 5 | — |
| above 100 | 12 | 4 | — | — |
| Total | 36 | 36 | 36 | 34 |

The third injection is given only to 34 patients because two patients cured by previous injection.

After one month, three months and six months, each patient was examined completely. Some patients were followed for one year. A prostatic smear was obtained each time and examined by wet film microscopically. Table 11 shows the results of the follow up.

TABLE 11

| Follow up | |
|---|---|
| Period of follow up | No. of cases |
| Three months | 15 |
| Six months | 10 |
| One year | 9 |
| Total | 34 |

Results of assessment

In assessing the results of treatment of chronic prostatitis with intraprostatic injection of zinc, twenty-two patients, out of the 36 cases, had been cured completely (subjective and objective). Eight patients exhibited improvement in their symptoms (which is partial improvement) with the number of leucocytes in their prostatic secretions markedly reduced compared to the pretreatment level. Six cases showed no improvement either subjectively or objectively.

TABLE 12

| Results of treatment | | |
|---|---|---|
| Results | No. of cases | % |
| Cure (subjective and objective) | 22 | 61.1 |
| Improvement | 8 | 22.2 |
| No improvement | 6 | 16.6 |
| Total | 36 | 100 |

Prostatic fluid culture after treatment

The 22 patients who were cured by intraprostatic injection of zinc, revealed sterile culture. As regards the eight cases who were improved, three of them still had the same organism as before treatment. Also three of the six patients who showed no improvement, revealed the same offending organisms as beforehand. This is shown in table 13.

TABLE 13

| Prostatic fluid culture after treatment | |
|---|---|
| Organisms | No. of cases |
| No growth | 30 |
| E. coli | 2 |
| B. Proteus | 2 |
| Enterococci | 1 |
| E. Coli + Ps. pyocyaneus | 1 |

This table shows that 9 out of 11 cases infected with E. coli were cured. On the other hand pseudomonas pyocyaneus and bacillus proteus organisms were insensitive to this type of treatment. Four out of five cases infected with Enterococci and the two cases who had Staphylococcus infection were also cured by zinc therapy.

In summary, 15 out of 21 patients with chronic bacterial prostatitis were cured and in the group of non bacterial prostatitis 7 out of 15 were cured demonstrating that intraprostatic zinc therapy is more effective in the treatment of bacterial prostatitis than the non bacterial type.

The zinc concentration in the serum separated from the blood was determined before and after treatment and compared with the zinc concentration in the blood drawn from 11 normal persons. Zinc concentration in these samples was determined by atomic absorption spectrophotometrically. The results were as follows:

Serum zinc concentration

The mean serum zinc concentration of the 11 normal subjects was found to be 84.6±19.8 ug.

The mean serum zinc in the untreated patients with chronic prostatitis was 49.2±5.2 ug. This shows that there is hypozincaemia in these patients. In addition, the free zinc in these patients was found to be tetrahedral.

The mean serum zinc after zinc injection was 123.9±24.1 ug demonstrating that the zinc level in the serum had been increased. The free zinc in these patients was also converted to octahedral.

EXAMPLE 2

Zinc acetate and zinc sulfate were administered orally to 24 patients. Zinc acetate is characterized by the fact that it is not a gastric irritant but both salts are easily soluble in water.

A solution of zinc acetate was prepared by dissolving 143 mg of zinc acetate in 100 ml of clean tap water in a clean container. Zinc sulfate was prepared in cachet form, each one containing 100 mg of zinc sulfate.

The solution of zinc acetate was given to 12 patients in a dose of 15 ml of the zinc acetate solution daily for 7 successive days. Hence each patient received 105 mg of zinc within this period.

The zinc sulfate was given to 12 patients in a dose of 100 mg three times a day for one week also.

Clinical assessment: Clinical assessment for every patient before and after treatment was performed as mentioned before.

Examination of prostatic discharge: A prostatic smear was examined for the number of leucocytes per high power field of microscope by wet and stained film. Culturing of the discharge was carried out and bacterial typing was done before treatment with both types of zinc. The results are reported in Table 14.

TABLE 14

| Prostatic smear before treatment | |
|---|---|
| No. of leucocytes/H.P.F. | No. of cases |
| 15–50 | 10 |
| 50–100 | 9 |
| Above 100 | 5 |
| Total | 24 |

Prostatic fluid culture before therapy

Culturing the prostatic secretions on blood agar revealed that there was no growth of any organisms in half of the cases. E. coli was found in about one third of the cases, whereas Klebsiella and Staphylococcus are found in 4 cases as seen in Table 15.

TABLE 15

| Prostatic fluid culture before therapy | |
|---|---|
| Organisms | No. of cases |
| No growth | 12 |
| E. coli | 8 |
| Klebsiella | 2 |
| Staphylococcus aureus | 2 |
| Total | 24 |

Urine culture

The urine was cultured on Mac Conkey media revealed that there is no growth of organisms in the great majority of cases. E. coli and Enterococci are found in some cases as seen in the Table 16.

TABLE 16

| Urine culture | |
|---|---|
| Organisms | No. of cases |
| No growth | 19 |
| E. coli | 4 |
| Enterococci | 1 |
| Total | 24 |

Serum zinc: Estimation of serum zinc before treatment by collection and separation of serum as mentioned before, was carried out. Also the same procedure was repeated for detection of serum zinc after treatment. The serum zinc before administration of zinc sulfate and zinc acetate orally was found to be 49.2±5.2 ug. After treatment with zinc sulfate, it was found to be nearly the same as before treatment but the mean serum zinc after treatment with zinc acetate was 123.9±24.1 ug.

Both groups who were treated with oral zinc sulfate and zinc acetate are grouped together, because there was no difference between them, except in the serum zinc which was raised in the group treated with zinc acetate.

Clinically

There was no improvement, the symptoms and physical findings were nearly the same as before treatment. The study of prostatic secretions by wet and stained films and the bacteriologic cultures also revealed that there was no appreciable changes.

EXAMPLE 3

In this study 18 patients with chronic prostatitis were studied.

The cases were diagnosed by clinical assessment, as well as by examination of prostatic fluid by wet and stained films. Also cultures of this secretion on aerobic blood agar and antibiogram were made.

Antibacterial agents: The antibacterial agents used in this group were, trimethoprim-sulfamethoxazole (80 mg and 400 mg, respectively), cephalosporine, tetracycline and erythromycin. These drugs were given in full dosage for 2 weeks accompanied with prostatic massage.

Prostatic massage: Prostatic massage was done twice weekly for five weeks coincidentally with antibacterial agents. The procedure was to massage the prostate in the lateral to medial direction, from both sides, then from above-downwards.

Assessments: After treatment, clinical assessment as well as examination of prostatic secretion by wet and stained films and also by culture was done.

Cure was obtained in 5 out of 18 patients. Two cases still had more than 100 leucocytes/H.P.F. of prostatic secretion compared to three cases before treatment. The results are shown in Table 17.

TABLE 17

| Leucocytes in prostatic smear | | |
|---|---|---|
| No. of leucocytes/H.P.F | No. cases before treatment | No. cases after treatment |
| Below 15 | — | 5 |

TABLE 17-continued

| Leucocytes in prostatic smear | | |
|---|---|---|
| No. of leucocytes/H.P.F | No. cases before treatment | No. cases after treatment |
| 15-50 | 8 | 5 |
| 50-100 | 7 | 6 |
| Above 100 | 3 | 2 |
| Total | 18 | 18 |

Urine culture

A urine sample was cultured on Mac Conkey's media and sterile urine was found in most cases. *E. coli* was found in 2 cases, *Pseudomonas aeroginosa* in one case and mixed infection by *E. coli* and enterococci in one case. These organism are the same organisms which are found in prostatic secretion.

TABLE 18

| Urine culture | |
|---|---|
| Organisms | No of cases |
| No growth | 14 |
| E. coli | 2 |
| Pseudomonas aeroginosa | 1 |
| E. coli + Enterococci | 1 |
| Total | 18 |

TABLE 19

| Bacteriologic culture after treatment | |
|---|---|
| Type of organisms | No. of cases |
| No growth | 12 |
| E. coli | 3 |
| Enterococci | 2 |
| Pseudomonas aeroginosa | 1 |

Of these 12 cases with no bacterial growth, 5 cases were cured and added to the 7 cases who are originally with no growth.

The relationship of bacteriologic culture before and after treatment is shown in Table 20.

TABLE 20

| Correlation of culture before and after treatment | | |
|---|---|---|
| Type of organisms | No. cases before treatment | No. cases after treatment |
| No growth | 7 | 12 |
| E. coli | 6 | 3 |
| Enterococci | 2 | 2 |
| Pseudomonas aeroginosa | 1 | 1 |
| Proteus | 1 | — |
| E. coli + Enterococci | 1 | — |
| Total | 18 | 18 |

Results of treatment. Five cases were cured (subjective and objective) where the number of leucocytes reduced to below 15 H.P.F, four cases improved (subjective) with a decrease of leucocytes in the prostatic secretion (objective), but 9 cases showed no improvement either subjectively or objectively. The results are shown in Table 21.

TABLE 21

| Results of treatment | | |
|---|---|---|
| Results of treatment | No. of cases | % |
| Cured | 5 | 27.8 |
| Improved | 4 | 22.2 |

TABLE 21-continued

| Results of treatment | | |
|---|---|---|
| Results of treatment | No. of cases | % |
| Not improved | 9 | 50 |

EXAMPLE 4

Four patients diagnosed with early prostatic carcinoma (Phase 1) with a history of prostatitis were treated as follows: An illuminated endoscope with a 50 cm catheter having a needle at one end was inserted through the urethra. Progress of the needle was monitored through the endoscope and by ultrasonography. The needle was focused towards and inserted into the prostate. One ml of an aqueous 6% by weight solution of zinc tannate was injected into the prostate through a syringe connected to the opposite end of the catheter.

The patients have been followed for 4 months as of the date of writing and have had no increase in the size of the prostate as documented by palpation and ultrasonography. All of the patients had difficulty urinating before treatment and three out of the four reported that they had less difficulty after one month and the fourth after 7 weeks.

In view of the above, it will be seen that the several objects of the invention are achieved and other advantageous results attained. As various changes could be made in the above methods without departing from the scope of the invention, it is intended that all matter contained in the above description or shown in the accompanying drawings shall be interpreted as illustrative and not in a limiting sense.

What is claimed:

1. A method of increasing the amount of prostatic antibacterial factor and inhibiting the rate of prostatic growth in a male animal having a compact or solid prostate which comprises injecting zinc ions from a zinc salt having a physiologically acceptable anion into the prostate in an amount effective to increase the amount of prostatic antibacterial factor and to limit the rate of prostatic growth, said ions injected in a solution in a volume from about 0.25 cc to 2 cc and a concentration equivalent to about 0.25% to 20% by weight $ZnSO_4 \cdot 7H_2O$ as $ZnSO_4 \cdot 7H_2O$ or as some other suitable zinc salt.

2. The method of claim 1 wherein the prostate is of a human male and the zinc ions are injected in aqueous solution in a volume about 0.25 cc to 2 cc.

3. The method of claim 2 wherein the zinc ions are present in an amount equivalent to about 1% to 2% by weight $ZnSO_4 \cdot 7H_2O$ as $ZnSO_4 \cdot 7H_2O$ or as some other suitable zinc salt and are injected in aqueous solution in a volume about 0.5 cc to 1 cc.

4. A method of increasing the amount of prostatic antibacterial factor and inhibiting the rate of prostatic growth in treating prostatitis in a human male which comprises the intraprostatic injection of zinc ions from a zinc salt having a physiologically acceptable anion in an amount effective to increase the amount of prostatic antibacterial factor and to inhibit the rate of prostatic growth, said ions injected in solution in a volume from about 0.25 cc to 2 cc and a concentration equivalent to about 0.25% to 20% by weight $ZnSO_4 \cdot 7H_2O$ as $ZnSO_4 \cdot 7H_2O$ or as some other suitable zinc salt.

5. The method of claim 4 wherein the zinc salt is selected from the group consisting of zinc acetate, zinc ascorbate, zinc chloride, zinc citrate, zinc gallate, zinc gluconate, zinc lactate, zinc salicylate, zinc sulfate, zinc tannate, zinc tartrate, zinc lysate, zinc arginate and zinc histidinate.

* * * * *